United States Patent
Lee et al.

(10) Patent No.: US 8,110,716 B2
(45) Date of Patent: Feb. 7, 2012

(54) METHOD FOR THE REMOVAL OF ACETYLENES FROM OLEFINS USING IONIC LIQUID-BASED SOLUTION

(75) Inventors: Hyun Joo Lee, Seoul (KR); Byoung Sung Ahn, Seoul (KR); Hoon Sik Kim, Seongbuk-gu (KR); Jin Hyung Kim, Seoul (KR); Jung Min Lee, Dobong-gu (KR)

(73) Assignee: Kolon Industries Inc., Gyeonggi-Do (KR)

( * ) Notice: Subject to any disclaimer, the term of this patent is extended or adjusted under 35 U.S.C. 154(b) by 441 days.

(21) Appl. No.: 12/250,143

(22) Filed: Oct. 13, 2008

(65) Prior Publication Data
US 2010/0030007 A1 Feb. 4, 2010

(30) Foreign Application Priority Data
Jul. 31, 2008 (KR) .......................... 10-2008-0075294

(51) Int. Cl.
*C07C 7/148* (2006.01)
(52) U.S. Cl. ........................................ 585/849; 585/860
(58) Field of Classification Search .................. None
See application file for complete search history.

(56) References Cited

U.S. PATENT DOCUMENTS

| | | |
|---|---|---|
| 3,755,448 A | 8/1973 | Merianos et al. |
| 3,758,603 A | 9/1973 | Steigelmann et al. |
| 3,792,981 A | 2/1974 | Hettick et al. |
| 4,034,065 A | 7/1977 | Kasai et al. |
| 4,318,714 A | 3/1982 | Kimura et al. |
| 4,717,398 A | 1/1988 | Pearce |
| 6,623,659 B2 * | 9/2003 | Munson et al. ............... 252/184 |
| 2003/0125599 A1 | 7/2003 | Boudreau et al. |

FOREIGN PATENT DOCUMENTS

DE 2059794 6/1971

OTHER PUBLICATIONS

Office action issued by Korean Patent Office on Jun. 18, 2010 for counterpart Korean application.
Safarik, Douglas J. et al.: "Olefin/Paraffin Separations by Reactive Absorption: A Review", *Ind. Eng Chem. Res.* 1998, 37, pp. 2571-2581.

* cited by examiner

*Primary Examiner* — Tam M Nguyen
(74) *Attorney, Agent, or Firm* — Frommer Lawrence & Haug LLP; Ronald R Santucci

(57) ABSTRACT

The present invention relates to a process for removing acetylenes from olefins by using an ionic liquid-based solution, and particularly to a process for removing a small amount of acetylenes contained in olefins by using an ionic liquid-based solution where copper halide (CuX, X=halogen atom) is dissolved. In an ionic liquid-based solution used in the present invention, copper halide (CuX) is stabilized by ionic liquid, thus preventing monovalent copper ion ($Cu^+$) from being oxidized into divalent copper ion ($Cu^{2+}$), maintaining the superior activity of monovalent copper ion ($Cu^+$) in removing acetylene for a long period of time, and remarkably increasing the selective removal of acetylene-based compounds. Moreover, an ionic liquid-based solution used in the present invention may serve as an extracting solution as well as an absorbent, thereby facilitating the operation and reducing equipment cost in comparison to the conventional extracting agent used in a slurry phase.

14 Claims, No Drawings

METHOD FOR THE REMOVAL OF ACETYLENES FROM OLEFINS USING IONIC LIQUID-BASED SOLUTION

CROSS-REFERENCE TO RELATED APPLICATION

This application claims under 35 U.S.C. §119(a) the benefit of Korean Patent Application No. 10-2008-0075294 filed Jul. 31, 2008, the entire contents of which are incorporated herein by reference.

BACKGROUND (a) Technical Field

The present invention relates to a process for removing acetylenes from olefins by using an ionic liquid-based solution, and particularly to a process of efficiently removing a small amount of acetylenes contained in olefins by using an ionic liquid-based solution where copper halide (CuX, X=halogen atom) is completely dissolved.

(b) Background Art

Olefins are obtained mainly by cracking naphtha or natural gas. However, it requires a rather complex purification process to obtain pure olefins because acetylenic compounds with similar boiling points are produced along with paraffinic hydrocarbons during the cracking process. The acetylenic compounds serve as poison in the process of producing polyolefins and can also lower the product quality. The acetylenic compounds are often converted into solid during the polymerization process, thus blocking the fluid stream and even leading to explosion. For this reason, it is necessary to remove even a small amount of acetylenic compound contained in olefins.

The commercial processes employ catalytic hydrogenation of acetylenes to obtain olefins therefrom. However, olefins produced from the hydrogenation of acetylenes as well as feed olefin can undergo further hydrogenation reaction to produce paraffins, thus resulting in the loss of olefins. Therefore, the removal of acetylenic compounds by using hydrogenation requires a catalyst that can selectively hydrogenate acetylenes. Although catalyst prepared by impregnating palladium impregnated on α-alumina is widely used, additional step for recycling the catalyst is required as disclosed in U.S. Pat. Nos. 3,755,448 and 3,792,981 because a relatively high hydrogenation activity results in the overproduction of paraffins and serious catalyst poisoning is caused by carbon deposit.

Examples of the conventional process of removing acetylenic compounds include the low temperature distillation, the liquid absorption, the solid absorption and the membrane separation in addition to the hydrogenation reaction. The low temperature distillation and the liquid absorption are widely used for separating unsaturated compound such as monoxide and olefins from gas mixture. However, he low temperature distillation requires high cost for equipments and high cost for their operation. The conventional liquid absorption method is also disadvantageous in an economic aspect due to the significant solvent loss.

Although U.S. Pat. Nos. 4,019,879 and 4,034,065 disclose a process for removing unsaturated compound such as carbon monoxide by adsorbing them with molecular sieves, adsorption capacity is limited and this process requires high vacuum during desorption step. U.S. Pat. No. 4,717,398 discloses a process for removing an unsaturated compound by using a faujasite-type zeolite substituted with $Cu^+$ and a pressure swing adsorption method. However, acetylenic compound can react with $Cu^+$ or $Ag^+$, thus producing unstable and explosive copper-acetylide or silver-acetylide.

German patent No. 2,059,794 discloses a process for removing unsaturated compound containing acetylenes by using a liquid-phase absorbent comprising monovalent copper compound and alkanol amine (e.g., monoethanol amine) as main ingredients. However, this process requires an additional purification process because final product is often contaminated by an alkanol amine. *Ind. Eng. Chem. Res.* 2571 (1998) also discloses a process of separating unsaturated compounds from paraffin mixtures by using a solution comprising silver or copper salt, which reversibly reacts with olefin and acetylene. However, the recycle of the solution requires a complicated and difficult process.

U.S. Pat. No. 3,758,603 discloses a process of separating unsaturated compounds and compounds by using a liquid membrane prepared by impregnating silver salt in a microporous membrane. However, according to this liquid-membrane method, it is difficult to maintain the separation efficiency for a long period of time because a facilitated transport carrier salt can be lost by the introduction of gas and solvent is easily evaporated. U.S. Pat. No. 4,318,714 discloses an ion exchange resin membrane having cations substituted with silver ion ($Ag^+$) for preventing the loss of silver ion. However, this membrane requires the supply of a certain level of water during the separation to facilitate the transportation of target compounds. This membrane is also disadvantageous in that the water contained in the permeated olefins should be removed after the separation.

SUMMARY OF THE DISCLOSURE

The present invention aims to overcome the aforementioned problems of the conventional process for removing acetylenes contained in olefins.

The present invention also aims to provide a solution for effectively removing acetylenes that can maintain a superior performance of removing acetylene even after a long-term operation.

The present invention overcomes the conventional problems mentioned above by providing a process of efficiently removing acetylenes contained in olefins using an ionic liquid-based solution comprising one or more ionic liquid selected from the group consisting of imidazolium compounds of Formula 1, and a copper halide (CuX; X is a halogen atom):

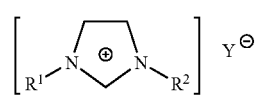

[Formula 1]

wherein $R^1$ and $R^2$ are independently a $C_1$-$C_6$ alkyl or $C_1$-$C_6$ alkoxy group; Y is selected from the group consisting of a halogen ion, a phosphite ion $[R^3OPH(O)O]^-$ and a phosphate ion $[(R^3O)_2P(O)O]^-$; and $R^3$ is a $C_1$-$C_6$ alkyl group.

Further, the present invent also overcomes the conventional problems mentioned above by providing a process for removing acetylenes contained in olefins using the ionic liquid-based solution comprising 5-40 wt % of the copper halide (CuX) relative to the ionic liquid of Formula 1.

The present invention also overcomes the conventional problems mentioned above by providing a process for removing acetylenes contained in olefins using an ionic liquid-based solution comprising a copper-containing ionic liquid of Formula 2, which is formed by the reaction between the ionic liquid of Formula 1 and copper halide (CuX):

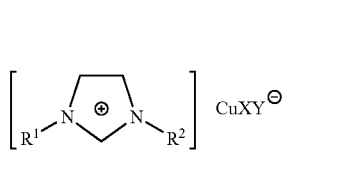

[Formula 2]

wherein $R^1$, $R^2$, X and Y are the same as defined in claim 1.

Further, according to an embodiment of the present invention, the amount of olefins to be treated with respect to the ionic liquid-based solution is 0.2-5 times more than that of the ionic liquid-based solution, thereby overcoming the problems in the conventional methods mentioned above.

According to another embodiment of the present invention, acetylenes are removed from olefins at 0-100° C., thereby overcoming the conventional problems mentioned above.

According to still another embodiment of the present invention, $C_5$-$C_8$ acetylenes contained in olefins, particularly isopropenyl acetylene, 1-hexyne, 1-heptyne and phenyl acetylene are removed from olefins at 0-100° C., thereby overcoming the problems in conventional methods mentioned above.

According to a further embodiment of the present invention, the ionic liquid-based solution used in the removal of the acetylenes is degassed for recycle at 20-120° C. and 1-200 mmHg.

An ionic liquid-based solution used in the present invention, where copper halide (CuX) is stabilized by ionic liquid, is effective in preventing monovalent copper ion ($Cu^+$) from being oxidized into divalent copper ion ($Cu^{2+}$).

An ionic liquid-based solution used in the present invention maintains the superior activity of monovalent copper ion ($Cu^+$) in removing acetylenes for a long period of time.

An ionic liquid-based solution used in the present invention maintains superior effect of removing acetylenes contained in olefins, particularly isopropenyl acetylene, 1-hexyne, 1-heptyne and phenyl acetylene.

DETAILED DESCRIPTION

Reference will now be made in detail to the preferred embodiments of the present invention, examples of which are illustrated in the drawings attached hereinafter, wherein like reference numerals refer to like elements throughout. The embodiments are described below so as to explain the present invention by referring to the figures.

An ionic liquid-based solution according to the present invention comprises imidazolium compound of Formula 1 and copper halide (CuX). Imidazolium compound of Formula 1 is required to completely dissolve copper halide (CuX), and one or more imidazolium compound of Formula 1 can be used in the present invention.

Further, imidazolium compound of Formula 1 and copper halide (CuX) comprised in an ionic liquid-based solution according to the present invention can be in the form of an ionic compound of Formula 2 produced by the reaction between imidazolium compound of Formula 1 and copper halide (CuX) as shown below:

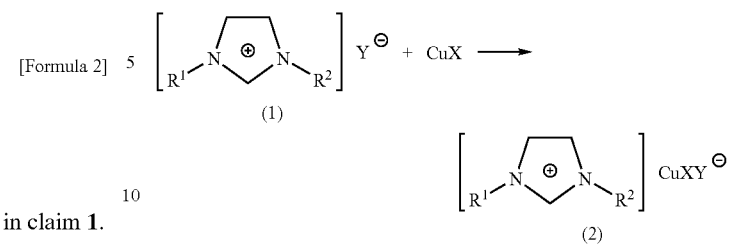

Scheme 1 wherein $R^1$, $R^2$, X and Y are the same as defined above.

An ionic compound of Formula 2 produced by the reaction between imidazolium compound and copper halide (CuX) is a different form of ionic liquid that can be dissolved in imidazolium compound of Formula 1. Copper halide (CuX) exists in a stabilized form of ionic compound of Formula 2 after the reaction with imidazolium compound, and is therefore prevented from being oxidized into divalent copper ion ($Cu^{2+}$).

Copper halide (CuX) is generally hardly dissolved in organic solvents, readily oxidizes upon reaction with alcohol, amine, etc., and produces explosive copper acetylide as a result of the reaction with acetylenes. Further, due to its similar binding affinities with a double bond compound and a triple bond compound, copper halide (CuX) is not very effective for selectively removing acetylenes from olefins.

In contrast, an ionic compound of Formula 2 produced by the reaction between imidazolium compound and copper halide (CuX) is resistant to oxidation compared to monovalent copper halide (CuX), and also shows a relatively weak interaction with the hydrogen atom or atoms in an acetylenic compound, thus producing no acetylide. Moreover, CuXY contained in an ionic compound of Formula 2 shows much stronger affinity to a triple-bond compound than to a double-bond compound, thereby significantly increasing the performance of selective removal of acetylenes contained in olefins.

Furthermore, an ionic liquid-based solution used in the present invention is immiscible with hydrocarbons such as paraffins, olefins or acetylenes, and can thus be easily separated from hydrocarbons through a simple layer separation. Hydrocarbons, particularly olefins and acetylenes contained in the separated ionic liquid-based solution are weakly bound, and can easily be removed by degassing under vacuum or at a relatively high temperature. After this simple process, an ionic liquid-based solution herein can be recycled and reused.

An ionic liquid-based solution of the present invention comprises copper halide (CuX) in the amount of 5-40 wt %, preferably 10-25 wt % relative to the amount of imidazolium compound of Formula 1. When the amount of copper halide (CuX) in ionic liquid-based solution is below the range, the efficiency of removing acetylenes can be insufficient. When the amount is too high, the viscosity of the solution can be increased, which can cause difficulty in performing the process.

The amount of olefins to be treated with respect to that of ionic liquid-based solution for removing acetylenes contained in olefins is 0.2-5 times, preferably 0.5-2 times. When the amount of olefins is too small, the productivity can be lowered. Larger amounts of olefins can result in unsatisfactory removal of acetylenes, and thus may require multi-step process.

Acetylenes contained in olefins are removed by extraction or absorption process. Since olefins having five or more carbons are liquids at room temperature, acetylenes can also be removed by a liquid-phase extraction at room temperature. Acetylenes can also be removed by evaporating olefins.

The extraction or absorption for removing acetylenes contained in olefins can be conducted at 0-100° C., preferably 20-50° C. Any temperature outside the above range can consume unnecessary energy, thus increasing production cost.

The present invention also relates to the recycle or reuse of ionic liquid-based solution used in removing acetylenes contained in olefins. Although the recycle temperature depends on the degassing conditions, a temperature of 20-120° C. is preferred, and 50-100° C. is more preferred. When the recycle temperature is too high, the recycling efficiency can be lowered. When the recycle temperature is too high, ionic compound of Formula 2 can be partially decomposed. Although degassing can be conducted under vacuum of 1-200 mmHg, 50-100 mmHg is preferred in an industrial respect. When the degree of vacuum is too high, the degassing efficiency can be lowered. On the other hand, when the degree of vacuum is too high, energy consumption will increase.

EXAMPLES

The following examples illustrate the invention and are not intended to limit the same.

Preparation Examples

Preparation of Ionic Liquid

Ionic liquid used in the present invention was prepared by reacting 1-alkylimidazole with alkyl halide, dialkylphosphite $[(R^3O)_2PH(=O)]$ or trialkylphosphate $[(R^3O)_3P=O]$. Although representative preparation methods of ionic liquids are described in Preparation Examples below, the present invention is not limited to the following Preparation Examples.

Preparation Example 1

Synthesis of 1-butyl-3-ethylimidazolium ethyl phosphite

1-Butylimidazole (60 g) and diethylphosphite (67 g) were added into a 500 mL two-necked flask with a reflux condenser, and mixed at 120° C. for 12 hours. After the reaction was completed, the products were washed with ethylacetate or diethylether several times to remove unreacted 1-butylimidazole and diethylphosphite, followed by vacuum drying at 60° C., thereby providing the title ionic liquid (yield 93%).

Among ionic liquids of Formula 1, dialkylimidazolium alkylphosphite can be prepared according to Preparation Example 1.

Preparation Example 2

Synthesis of 1-ethyl-3-methylimidazolium diethyl phosphate

1-Methylimidazole (60 g) and triethylphosphite (133 g) were added into a 500 mL two-necked flask with a reflux condenser, and mixed at 120° C. for 12 hours. After the reaction was completed, the products were washed with ethylacetate or diethylether several times to remove unreacted 1-methylimidazole (60 g) and triethylphosphite, followed by vacuum drying at 60° C., thereby providing the title ionic liquid (yield 98%).

Among ionic liquids of Formula 1, dialkylimidazolium alkylphosphite can be prepared according to Preparation Example 2.

Examples

Removal of Acetylenes Contained in Olefins

Acetylenes contained in olefins were removed by using ionic liquid-based solution according to the present invention as described below. However, the present invention is not limited to the following Examples.

Example 1

Isoprene (1 g) containing 1,000 ppm of isopropenyl acetylene (IPA) and 1,000 ppm of 2-butyne (2-BT), and 5,000 ppm of n-heptane as an internal standard was mixed with the ionic liquid-based solution (2.0 g) of CuCl (0.4 g) dissolved in 1-butyl-3-ethylimidazolium ethylphosphite prepared in Preparation Example 1.

The resulting mixture was vigorously stirred for 1 min at 25° C., and then separated into two layers. The separated upper organic and lower ionic liquid layers were analyzed by using GC (Agilent, 6890N, HP-PLOT column) and $^1$H NMR (Brucker, 400 MHz NMR).

The analysis showed that IPA, 2-BT and isoprene were extracted in yields of 100%, 31% and 0.08%, respectively.

Examples 2-10

IPA and 2-BT contained in isoprene were removed using the same as in Example 1 except that a different kind of ionic liquid of Formula 1 was used as presented in Table 1. The degree of extraction of acetylenes is shown in percentage in Table 1.

TABLE 1

| | Ionic liquid (Formula 1) | | | Degree of extraction (%) | |
|---|---|---|---|---|---|
| Example | $R^1$ | $R^2$ | Y | IPA | 2-BT |
| 2 | $CH_3$ | $C_2H_5$ | $OP(=O)(H)(OC_2H_5)$ | 97 | 26 |
| 3 | $CH_3$ | $C_4H_9$ | $OP(=O)(H)(OC_4H_9)$ | 100 | 26 |
| 4 | $C_4H_9$ | $CH_3$ | $OP(=O)(H)(OCH_3)$ | 100 | 28 |
| 5 | $n\text{-}C_6H_{11}$ | $CH_3$ | $OP(=O)(H)(OC_6H_{11})$ | 100 | 27 |
| 6 | $CH_3$ | $n\text{-}C_6H_{11}$ | $OP(=O)(H)(OCH_3)$ | 100 | 28 |
| 7 | $CH_3$ | $CH_3$ | $OP(=O)(OCH_3)_2$ | 94 | 24 |
| 8 | $CH_3$ | $C_2H_5$ | $OP(=O)(OC_2H_5)_2$ | 94 | 23 |
| 9 | $C_4H_9$ | $CH_3$ | $OP(=O)(OC_4H_9)_2$ | 94 | 23 |
| 10 | $CH_3$ | $n\text{-}C_6H_{11}$ | $OP(=O)(OCH_3)_2$ | 95 | 25 |
| 11 | $CH_3$ | $C_4H_9$ | Cl | 75 | 26 |

IPA: isopropenyl acetylene;
2-BT: 2-butyne

Examples 12-18

IPA and 2-BT contained in isoprene were removed the same as in Example 1 except that a different amount of CuCl was used as presented in Table 2. The removal of acetylenes is shown in percentage in Table 2.

TABLE 2

| Example | CuCl (wt. %)* | Degree of extraction (%) | |
|---|---|---|---|
| | | IPA | 2-BT |
| 12 | 5 | 75 | 19 |
| 13 | 10 | 95 | 26 |
| 14 | 15 | 100 | 28 |
| 15 | 20 | 100 | 31 |
| 16 | 25 | 100 | 35 |
| 17 | 30 | 100 | 39 |
| 18 | 40 | 100 | 45 |

*wt. %: amount CuCl relative to ionic liquid (1-butyl-3-ethylimidazolium ethylphosphite)

Examples 19-20

IPA and 2-BT contained in isoprene were removed the same as in Example 1 except that CuBr or CuI was used instead of CuCl as presented in Table 3. The removal of acetylenes is shown in percentage in Table 3.

TABLE 3

| Example | Copper halide (CuX) | Degree of extraction (%) | |
|---|---|---|---|
| | | IPA | 2-BT |
| 17 | CuBr | 100 | 35 |
| 18 | CuI | 100 | 38 |

Examples 21-23

IPA and 2-BT contained in isoprene liquid of Formula 1 were used as presented in Table 4. The removal of acetylenes is shown in percentage in Table 4.

TABLE 4

| Example | Ionic liquid (Formula 1) | | Degree of extraction (%) | |
|---|---|---|---|---|
| | A | B | IPA | 2-BT |
| 21 | 1-Butyl-3-ethylimidazolium ethylphosphite | 1-Ethyl-3-methylimidazolium ethylphosphite | 98 | 27 |
| 22 | 1-Butyl-3-methylimidazolium butylphosphite | 1-Ethyl-3-methylimidazolium methylphosphite | 95 | 25 |
| 23 | 1-Butyl-3-ethylimidazolium ethylphosphite | 1,3-Dimethylimidazolium dimethylphosphate | 94 | 25 |

Examples 24-29

IPA and 2-BT contained in isoprene were removed the same as in Example 1 except that the amount of olefin specimen was changed as presented in Table 5. The removal of acetylenes is shown in percentage in Table 5.

TABLE 5

| Example | Wt. of feed (g)* | Degree of extraction (%) | |
|---|---|---|---|
| | | IPA | IPA |
| 24 | 0.20 | 100 | 48 |
| 25 | 0.50 | 100 | 31 |
| 26 | 1.00 | 83 | 25 |
| 27 | 1.50 | 79 | 21 |
| 28 | 2.00 | 75 | 18 |
| 29 | 5.00 | 53 | 13 |

*The amount of olefin feed relative to 1 g of an ionic-liquid-based solution

Examples 30-35

Acetylenes contained in olefins were removed the same as in Example 1 except that a different kind of olefin feed and ionic liquid was used as presented in Table 6.

Extractions of acetylenes were carried out with 1-hexene containing 1000 ppm of 1-hexyne, 1-heptene containing 1000 ppm of 1-heptyne, and a styrene feed containing 1000 ppm of phenyl acetylene, respectively using an ionic liquid-based extractant (2.0 g) consisting of CuCl (0.4 g) dissolved in an ionic liquid shown Table 6.

TABLE 6

| Example | Feed olefin | Ionic liquid | Degree of acetylene removal (%) |
|---|---|---|---|
| 30 | 1-Hexene | 1-Butyl-3-ethylimidazolium ethylphosphite | 100 |
| 31 | 1-Hexene | 1-Butyl-3-methylimidazolium dimethylphosphate | 97 |
| 32 | 1-Heptene | 1-Butyl-3-methylimidazolium butylphosphite | 100 |
| 33 | 1-Heptene | 1-Ethyl3-methylimidazolium ethylphosphite | 100 |
| 34 | Styrene | 1,3-dimethylimidazolium dimethylphosphate | 91 |
| 35 | Styrene | 1-Ethyl-3-methylimidazolium ethylphosphite | 96 |

Examples 36-40

IPA and 2-BT contained in isoprene were removed the same as in Example 1 except that the extraction was conducted at a different temperature as presented in Table 7. The removal of IPA and 2-BT is shown in percentage in Table 7.

TABLE 7

| Example | Extraction temperature (° C.) | Degree of extraction (%) | |
|---|---|---|---|
| | | IPA | 2-BT |
| 36 | 20 | 100 | 33 |
| 37 | 25 | 100 | 31 |
| 38 | 30 | 97 | 27 |
| 39 | 40 | 94 | 22 |
| 40 | 50 | 87 | 17 |

Examples 41-45

IPA and 2-BT contained in isoprene were extracted the same as in Example 1, and the extracted hydrocarbons in an ionic liquid including isoprene, IPA, and 2-BT were removed under a reduced pressure for the further reuse of the ionic liquid. The conditions and the results of regeneration are presented in Table 8.

TABLE 8

| Example | Regeneration condition | | Degree of extraction (%) | |
|---|---|---|---|---|
| | Temperature (° C.) | Pressure (mmHg) | IPA | 2-BT |
| 41 | 20 | 50 | 83 | 87 |
| 42 | 50 | 20 | 100 | 100 |
| 43 | 50 | 70 | 96 | 98 |
| 44 | 70 | 50 | 100 | 100 |
| 45 | 100 | 100 | 100 | 100 |

As described above, an ionic liquid-based extractant or absorbent disclosed in the present invention comprises copper halide (CuX, X=halogen atom) dissolved in ionic liquid. In an ionic liquid-based solution used in the present invention, copper halide (CuX) is stabilized by an ionic liquid, thus preventing monovalent copper ion ($Cu^+$) from being oxidized into divalent copper ion ($Cu^{2+}$), maintaining the superior activity of monovalent copper ion ($Cu^+$) in removing acetylenic compounds for a long period of time, and remarkably increasing the selective removal of acetylenic compounds. Moreover, an ionic liquid-based solution used in the present invention is a homogeneous liquid with no vapor pressure and therefore solvent loss can be neglected and the operation can be facilitated, thereby reducing equipment cost in comparison to the conventional process using a slurry phase extractant.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A process for removing acetylenes contained in olefins, comprising treating the olefins with an ionic liquid-based solution comprising one or more ionic liquid selected from the group consisting of imidazolium compounds of Formula 1, and a copper halide (CuX; X is a halogen atom):

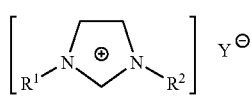

[Formula 1]

wherein $R^1$ and $R^2$ are independently a $C_1$-$C_6$ alkyl or $C_1$-$C_6$ alkoxy group; Y is selected from the group consisting of a phosphite ion [$R^3$OPH(O)O]— and a phosphate ion [($R^3$O)$_2$P(O)O]—; and $R^3$ is a $C_1$-$C_6$ alkyl group.

2. The process of claim 1, wherein the ionic liquid-based solution comprises 5-40 wt. % of the copper halide (CuX) relative to the ionic liquid of Formula 1.

3. The process of claim 2, wherein the ionic liquid-based solution comprises 10-25 wt. % of the copper halide (CuX) relative to the ionic liquid of Formula 1.

4. The process of claim 1, wherein the ionic liquid-based solution comprises a copper-containing ionic liquid of Formula 2:

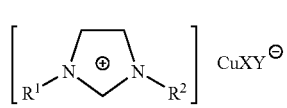

[Formula 2]

wherein $R^1$, $R^2$, X and Y are the same as defined in claim 1.

5. The process of claim 1, wherein the amount of the olefins is 0.2-5 times higher in weight than that of the ionic liquid-based solution.

6. The process of claim 5, wherein the amount of the olefins is 0.5-2 times higher in weight than that of the ionic liquid-based solution.

7. The process of claim 1, wherein the treating is conducted at 0-100° C.

8. The process of claim 7, wherein the treating is conducted at 20-50° C.

9. The process of claim 1, wherein the acetylenes is a C5-C8 acetylenic compound.

10. The process of claim 9, wherein the acetylene is selected from the group consisting of isopropenyl acetylene, 1-hexyne, 1-heptyne and phenyl acetylene.

11. The process of claim 1, wherein the ionic liquid-based solution used in the removal of the acetylenes is regenerated at 20-120° C. and 1-200 mmHg.

12. The process of claim 11, wherein the ionic liquid-based solution used in the removal of the acetylenes is regenerated at 50-100° C. and 50-100 mmHg.

13. The process or claim 2, wherein the ionic liquid-based solution comprises a copper-containing ionic liquid of Formula 2:

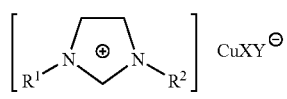

[Formula 2]

wherein $R^1$, $R^2$, X and Y are the same as defined in claim 1.

14. The process of claim 3, wherein the ionic liquid-based solution comprises a copper-containing ionic liquid of Formula 2:

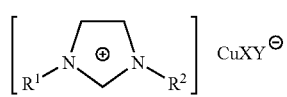

[Formula 2]

wherein $R^1$, $R^2$, X and Y are the same as defined in claim 1.

* * * * *